United States Patent
Okazaki et al.

(10) Patent No.: US 10,278,566 B2
(45) Date of Patent: May 7, 2019

(54) CONTROL DEVICE AND MEDICAL IMAGING SYSTEM

(71) Applicants: SONY CORPORATION, Tokyo (JP); SONY OLYMPUS MEDICAL SOLUTIONS INC., Tokyo (JP)

(72) Inventors: Sakae Okazaki, Tokyo (JP); Hirotaka Hirano, Gifu (JP); Takahiro Yamamoto, Tokyo (JP)

(73) Assignees: SONY CORPORATION, Tokyo (JP); SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 15/564,928

(22) PCT Filed: May 10, 2016

(86) PCT No.: PCT/JP2016/063931
§ 371 (c)(1),
(2) Date: Oct. 6, 2017

(87) PCT Pub. No.: WO2016/185952
PCT Pub. Date: Nov. 24, 2016

(65) Prior Publication Data
US 2018/0084979 A1    Mar. 29, 2018

(30) Foreign Application Priority Data

May 18, 2015    (JP) .................................. 2015-100962

(51) Int. Cl.
*A61B 1/00*    (2006.01)
*A61B 1/04*    (2006.01)
(Continued)

(52) U.S. Cl.
CPC ............ *A61B 1/00188* (2013.01); *A61B 1/00* (2013.01); *A61B 1/04* (2013.01); *A61B 1/05* (2013.01);
(Continued)

(58) Field of Classification Search
CPC ....... A61B 1/00188; A61B 1/05; A61B 1/045; G02B 21/244; G02B 7/38; G02B 27/0075; H04N 5/23212; H04N 2005/2255
See application file for complete search history.

(56) References Cited

U.S. PATENT DOCUMENTS

2003/0040659 A1    2/2003 Kazakevich
2004/0130651 A1    7/2004 Wakashiro
(Continued)

FOREIGN PATENT DOCUMENTS

JP    5-232378 A    9/1993
JP    8-106060 A    4/1996
(Continued)

OTHER PUBLICATIONS

International Search Report dated Aug. 2, 2016, in PCT/JP2016/063931 filed May 10, 2016.
(Continued)

*Primary Examiner* — Twyler L Haskins
*Assistant Examiner* — Fayez Bhuiyan
(74) *Attorney, Agent, or Firm* — Oblon, McClelland, Maier & Neustadt, L.L.P.

(57) ABSTRACT

[Object] To make it possible to further improve convenience of a user.
[Solution] There is provided a control device including: an autofocus control section configured to execute an autofocus operation by moving at least one optical member; and an autofocus operation determination section configured to
(Continued)

determine whether it is possible for the autofocus operation to bring biological tissue into focus, the biological tissue serving as an object. In a case where the autofocus operation determination section determines that it is not possible for the autofocus operation to bring the object into focus, the autofocus control section moves the at least one optical member to a predicted focal position set in advance in accordance with a purpose of imaging.

20 Claims, 3 Drawing Sheets

(51) Int. Cl.
G02B 7/28 (2006.01)
H04N 5/232 (2006.01)
G02B 7/30 (2006.01)
G02B 7/34 (2006.01)
G02B 7/36 (2006.01)
A61B 1/05 (2006.01)
G02B 21/24 (2006.01)
A61B 1/045 (2006.01)
G02B 7/38 (2006.01)
G02B 27/00 (2006.01)
H04N 5/225 (2006.01)

(52) U.S. Cl.
CPC .............. *G02B 7/28* (2013.01); *G02B 7/30* (2013.01); *G02B 7/34* (2013.01); *G02B 7/36* (2013.01); *G02B 21/244* (2013.01); *H04N 5/23212* (2013.01); *A61B 1/045* (2013.01); *G02B 7/38* (2013.01); *G02B 27/0075* (2013.01); *H04N 2005/2255* (2013.01)

(56) References Cited

U.S. PATENT DOCUMENTS

2004/0178322 A1   9/2004   Kaneko et al.
2013/0016275 A1   1/2013   Hokoi
2013/0083180 A1*   4/2013   Sasaki ............... H04N 5/23212
                                                                              348/65
2015/0070566 A1   3/2015   Yoshida

FOREIGN PATENT DOCUMENTS

JP    2001-350082 A    12/2001
JP    2004-205981 A    7/2004
JP    2011-186452 A    9/2011

OTHER PUBLICATIONS

Extended Search Report dated Nov. 13, 2018, in European Patent Application No. 16796346.1-1020 / 3282296 PCT/JP2016063931; 9 pgs.

* cited by examiner

CONTROL DEVICE AND MEDICAL IMAGING SYSTEM

TECHNICAL FIELD

The present disclosure relates to a control device and a medical imaging system.

BACKGROUND ART

Endoscopic systems or microscopic systems (which will be generically referred to as imaging systems) are known as systems that image biological tissue of patients to allow the biological tissue to be observed at the time of surgical operations or inspections. Some of the imaging systems have autofocus (AF) functions of automatically bringing objects into focus. For example, Patent Literature 1 discloses a microscopic system that detects a light amount change in the light from an object, drive an optical system to execute an AF operation in a case where the light amount change falls within a predetermined range, and moves the optical system to an initial position without performing any AF operation in a case where the light amount change is beyond the predetermined range.

CITATION LIST

Patent Literature

Patent Literature 1: JP H5-232378A

DISCLOSURE OF INVENTION

Technical Problem

The technology described in Patent Literature 1, however, simply moves the optical system to the initial position in a case where the light amount change is beyond the predetermined range, namely in a case where it is determined that it is not possible to normally execute an AF operation. As a result, there is a high probability that an unclear image out of focus is acquired. To carry out surgical operations or inspections, a surgeon thus needs an additional operation such as manually adjusting the position of the optical system for focusing. In view of the above-described circumstances, an imaging system is requested that is more convenient for users.

The present disclosure then proposes a novel and improved control device and medical imaging system that can further improve the convenience of a user.

Solution to Problem

According to the present disclosure, there is provided a control device including: an autofocus control section configured to execute an autofocus operation by moving at least one optical member; and an autofocus operation determination section configured to determine whether it is possible for the autofocus operation to bring biological tissue into focus, the biological tissue serving as an object. In a case where the autofocus operation determination section determines that it is not possible for the autofocus operation to bring the object into focus, the autofocus control section moves the at least one optical member to a predicted focal position set in advance in accordance with a purpose of imaging.

Further, according to the present disclosure, there is provided a medical imaging system including: an image sensor configured to image biological tissue serving as an object; an optical system configured to concentrate light from the object on the image sensor, and configured in a manner that at least one optical member is movable on an optical axis for a focusing operation; an autofocus control section configured to execute an autofocus operation by moving the at least one optical member; and an autofocus operation determination section configured to determine whether it is possible for the autofocus operation to bring the object into focus. In a case where the autofocus operation determination section determines that it is not possible for the autofocus operation to bring the object into focus, the autofocus control section moves the at least one optical member to a predicted focal position set in advance in accordance with a purpose of imaging.

According to the present disclosure, in a case where it is determined through that it is not possible for an autofocus operation to bring an object into focus, at least one optical member (such as a focus lens) moved in the autofocus operation moves to a predicted focal position set in advance in accordance with the purpose of imaging. The position of the at least one optical member at which an object comes into focus in an object distance assumed in accordance with the purpose of imaging can be set as the predicted focal position on the basis of the object distance. The movement of the at least one optical member to the predicted focal position thus offers an image that has biological tissue serving as an object relatively in focus. A surgeon can therefore carry out a surgical operation or an inspection with no additional operation such as focusing, which can further improve the convenience of the surgeon.

Advantageous Effects of Invention

As described above, according to the present disclosure, it is possible to improve the convenience of a user. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
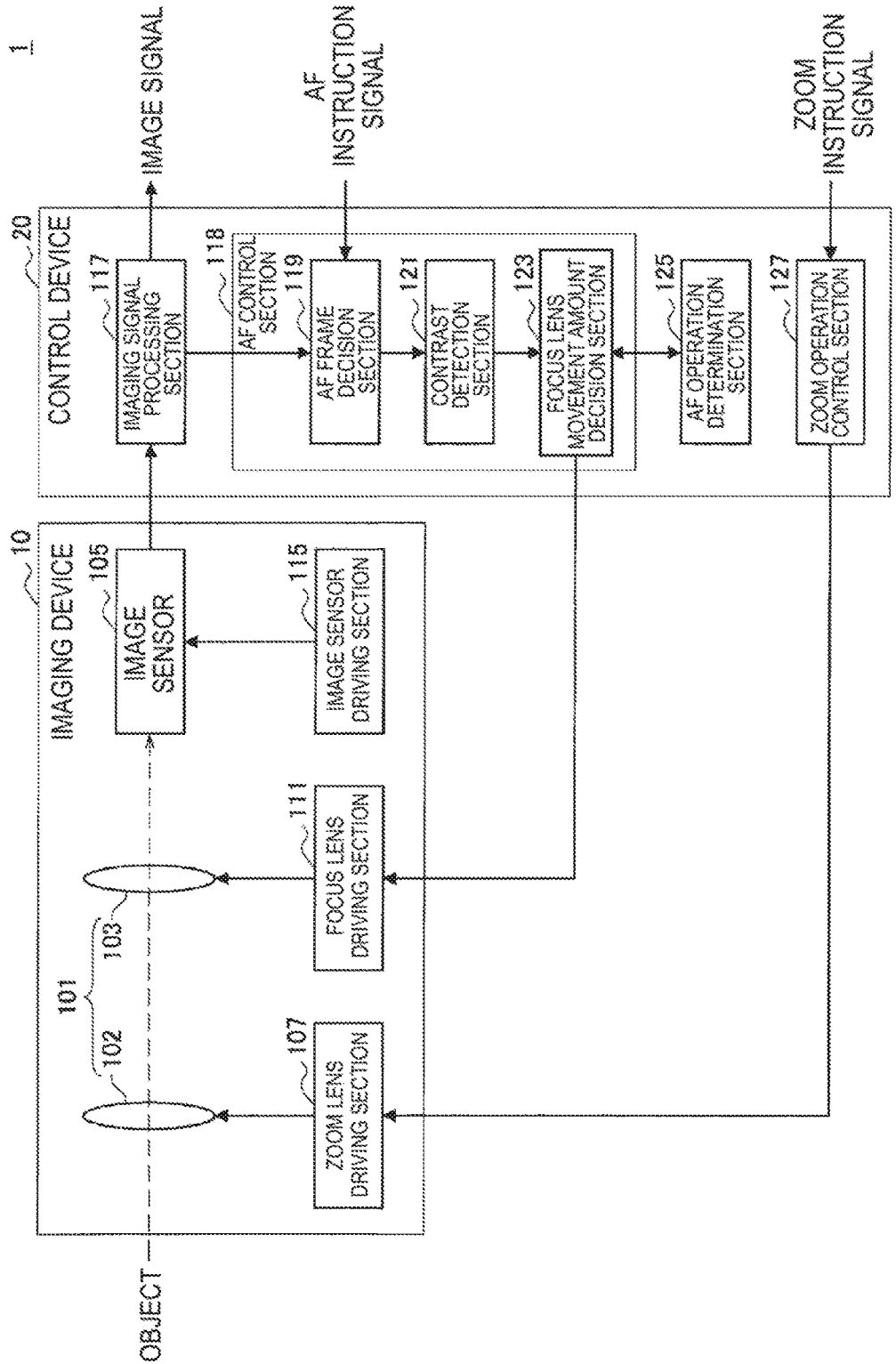
FIG 1 is a block diagram illustrating a configuration example of an imaging system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will be made in the following order.
1. Configuration of Imaging System
2. Imaging Method
3. Modifications
3-1. Case Where Phase Difference Method Is Used
3-2. Case Where Depth Map Method Is Used
3-3. Case Where Triangulation Method Is Used
4. Supplemental Information Additionally, the following describes, as a surgeon, a user who performs a variety of operations on an imaging system according to an embodiment of the present disclosure for the sake of convenience. The description does not, however, limit users who use the imaging system. A variety of operations on the imaging system may be executed by any user such as another medical staff member.

(1. Configuration of Imaging System)

The configuration of an imaging system according to an embodiment of the present disclosure will be described with reference to FIG. 1. FIG. 1 is a block diagram illustrating a configuration example of the imaging system according to the present embodiment.

FIG. 1 illustrates that an imaging system 1 according to the present embodiment includes an imaging device 10, and a control device 20 that performs various kinds of signal processing for the operation of the imaging device 10. The imaging system 1 is a medical imaging system 1, and has an objective of imaging the biological tissue of a patient at the time of a surgical operation or an inspection in the present embodiment. The imaging system 1 can be, for example, an endoscopic system or a microscopic system. An endoscope inserted into a body cavity of a patient images the biological tissue of the body cavity at the time of a surgical operation or an inspection in the endoscopic system. Meanwhile, an operative site is imaged by a microscopic section (including, for example, an optical system and an image sensor in a lens-barrel) supported above the operative site by a support arm or the like at the time of laparotomy or craniotomy in the microscopic system. A surgeon can carry out a surgical operation or an inspection while referring to an operative site or an inspection part imaged by an endoscopic section or the microscopic section.

FIG. 1 illustrates the configuration corresponding to the endoscopic system as an example of the imaging system 1. For example, the imaging device 10 corresponds to a camera head, and the control device 20 corresponds to a camera controll unit (CCU). The imaging device 10 is connected to the control device 20 by an optical fiber and/or an electrical signal cable. Various kinds of information can be transmitted and received through an optical signal and/or an electrical signal.

Additionally, FIG. 1 chiefly illustrates only components necessary for describing the present embodiment, but illustrates no other components. The imaging system 1 can, however, include various components of a typical endoscopic system such as an endoscope and a light source device that supplies the endoscope with illumination light with which biological tissue of a patient serving as an object is irradiated at the time of imaging.

An insertion section of the endoscope which is small in diameter is inserted into a body cavity of a patient at the time of imaging. The distal end of the insertion section of the endoscope is provided with an illumination window. An object is irradiated with illumination light supplied from the light source device through the illumination window. The distal end of the insertion section of the endoscope is also provided with an observation window through which reflected light (observation light) acquired by the illumination light being reflected from the object is acquired. The observation light acquired through the observation window is guided to the proximal end of the endoscope by a light guide member provided in the lens-barrel of the endoscope. The imaging device 10 (i.e., camera head) is attached to the proximal end of the endoscope. Observation light is collected by an image sensor 105 discussed below which is provided in the imaging device 10, thereby capturing an object image.

The following describes the configurations of the imaging deice 10 and the control device 20 in more detail. First, the configuration of the imaging device 10 will be described.

The imaging device 10 includes an optical system 101 and the image sensor 105. Further, the imaging device 10 includes a zoom lens driving section 107, a focus lens driving section 111, and an image sensor driving section 115 as functions thereof.

The optical system 101 concentrates, on the image sensor 105, the observation light guided through the endoscope. The optical system 101 includes a zoom lens 102 and a focus lens 103. Additionally, FIG. 1 representatively illustrates only the zoom lens 102 and the focus lens 103, but the optical system 101 may also include a variety of optical members such as another lens and filter. The type and number of optical members included in the optical system 101, the optical property of each optical member, and the like are adjusted as needed in a manner that the optical system 101 forms an object image on the light receiving surface of the image sensor 105.

The zoom lens 102 a lens for adjusting the magnification of the optical system 101. The zoom lens 102 is configured to be movable on the optical axis. The position of the zoom lens 102 on the optical axis is controlled, thereby adjusting the magnification of the optical system 101. Additionally, the zoom lens 102 is an example of optical members for adjusting the magnification of the optical system 101. As long as the position of at least one optical member included in the optical system 101 on the optical axis is adjusted, and the magnification of the optical system 101 is hereby adjusted, the number and type of optical members configured to be movable for adjusting the magnification are not limited in the present embodiment.

The focus lens 103 is a lens for adjusting the focal distance of the optical system 101. The focus lens 103 is configured to be movable on the optical axis. The position of the focus lens 103 on the optical axis is controlled, thereby adjusting the focal distance of the optical system 101. Additionally, the focus lens 103 is an example of optical members for adjusting the focal distance of the optical system 101. As long as the position of at least one optical member included in the optical system 101 on the optical axis is adjusted, and the focal distance of the optical system 101 is hereby adjusted, the number and type of optical members configured to be movable for adjusting the focal distance are not limited in the present embodiment.

The image sensor 105 images an object by receiving observation light on the light receiving surface thereof. Specifically, the image sensor 105 has a light receiving surface on which light receiving elements such as photodiodes are arranged. The image sensor 105 receives observation light on the light receiving surface, thereby acquiring an electrical signal corresponding to the observation light through photoelectric conversion, namely an imaging signal that is an electrical signal corresponding to an object image. The configuration of the image sensor 105 is not limited. A variety of known image sensors such as a charge coupled device (CCD) image sensor and a complementary metal-oxide-semiconductor (CMOS) image sensor may be used as the image sensor 105. The imaging signal acquired by the image sensor 105 is transmitted to an imaging signal processing section 117 of the control device 20 which will be described below.

The zoom lens driving section 107 includes, for example, a motor, a driver circuit that supplies a drive current to the motor, and the like. The zoom lens driving section 107 moves the zoom lens 102 along the optical axis. The operation of the zoom lens driving section 107 is controlled by a zoom lens drive control section that is not illustrated. The zoom lens drive control section includes a variety of processors such as a central processing unit (CPU) and a digital signal processor (DSP), or a microcomputer or the like in which the processor and a storage element such as a memory are both installed. The zoom lens drive control section controls the operation of the zoom lens driving section 107. The zoom lens drive control section may also include a variety of integrated circuits such as a field-programmable gate array (FPGA), a driver integrated circuit (IC), and/or a dedicated large-scale integration (LSI) (i.e., application specific integrated circuit (ASIC)). The function of the zoom lens drive control section can be implemented by the processor included in the zoom lens drive control section executing operational processing in accordance with a predetermined program.

Specifically, the zoom lens drive control section controls the driving of the zoom lens driving section 107 in accordance with the movement amount of the zoom lens 102 calculated by a zoom operation control section 127 of the control device 20 which will be described below, thereby moving the zoom lens 102 by the movement amount to adjust the magnification of the optical system 101. Additionally, in a case where an optical member other than the zoom lens 102 is also configured to be movable for adjusting the magnification of the optical system 101, the zoom lens driving section 107 may also move the other optical member on the optical axis under the control of the zoom lens drive control section.

Additionally, the configurations and functions of the zoom lens driving section 107 and the zoom lens drive control section may be similar to the configuration and function of a mechanism installed in a typical imaging device (such as a camera head of an endoscopic system) for implementing the zoom function. The configurations and functions of the zoom lens driving section 107 and the zoom lens drive control section will not be thus described in detail here.

The focus lens driving section 111 includes, for example, a motor, a driver circuit that supplies a drive current to the motor, and the like. The focus lens driving section 111 moves the focus lens 103 along the optical axis. The operation of the focus lens driving section 111 is controlled by a focus lens drive control section that is not illustrated. The focus lens drive control section includes a variety of processors such as a CPU and a DSP, a microcomputer, and the like. The focus lens drive control section control the operation of the focus lens driving section 111. The focus lens drive control section may also include a variety of integrated circuits such as a FPGA, a driver IC, and/or a dedicated LSI (i.e., ASIC). The function of the focus lens drive control section can be implemented by the processor included in the focus lens drive control section executing operational processing in accordance with a predetermined program.

Specifically, the imaging system 1 has an autofocus (AF) function. The focus lens drive control section controls the driving of the focus lens driving section 111 in accordance with the movement amount of the focus lens 103 calculated by an autofocus control section 118 (AF control section 118) of the control device 20 described below in accordance with a predetermined AF method, thereby moving the focus lens 103 by the movement amount to adjust the focal distance of the optical system 101. Additionally, in a case where an optical member other than the focus lens 103 is also configured to be movable for adjusting the focal distance of the optical system 101, the focus lens driving section 111 may also move the other optical member on the optical axis under the control of the focus lens drive control section.

Additionally, the configurations and functions of the focus lens driving section 111 and the focus lens drive control section may be similar to the configuration and function of a mechanism installed in a typical imaging device (such as a camera head of an endoscopic device) for implementing the AF function. The configurations and functions of the focus lens driving section 111 and the focus lens drive control section will not be thus described in detail here.

The image sensor driving section 115 corresponding to a driver for driving the image sensor 105. The image sensor driving section 115 supplies a driving signal (signal for driving a transistor or the like installed in the image sensor 105) to the image sensor 105 at predetermined timing, thereby causing the image sensor 105 to execute an operation such as an imaging operation or a reset operation at predetermined timing and acquire an imaging signal corresponding to an object image. Additionally, although not illustrated, an image sensor drive control section that controls the operation of the image sensor driving section 115 can be provided to the imaging device 10 or the control device 20. The image sensor drive control section includes a variety of processors such as a CPU and a DSP, a microcomputer, and the like. The image sensor drive control section instructs the image sensor driving section 115 about the timing at which the driving signal is supplied to the image sensor 105, thereby controlling the driving of the image sensor 105 via the image sensor driving section 115. Additionally, the function of the image sensor drive control section can be implemented by the processor included in the image sensor drive control section executing operational processing in accordance with a predetermined program.

The start and end of imaging can be controlled in accordance with an instruction issued by a surgeon via an input device such as a switch (not illustrated) in the imaging system 1. Specifically, the imaging system 1 includes an input device for receiving an instruction signal indicating the start of imaging. The image sensor drive control section controls the driving of the image sensor 105 in accordance with an instruction issued by a surgeon via the input device, and imaging can be hereby started and ended.

Additionally, the configurations and functions of the image sensor driving section 115 and the image sensor drive control section may be similar to the configuration and function of a mechanism installed in a typical imaging device (such as a camera head of an endoscopic device) for implementing the imaging function of the image sensor for imaging an object. The configurations and functions of the image sensor driving section 115 and the image sensor drive control section will not be thus described in detail here.

Additionally, the components corresponding to the above-described zoom lens drive control section, focus lens drive control section, and/or image sensor drive control section may be installed in the imaging device 10 or the control device 20. Further, although not illustrated, the control device 20 can include a connector (not illustrated) to which an optical fiber and/or an electrical signal cable used to exchange various kinds of information with the imaging devise 10 is connected. The connector may be configured in a manner that an integrated circuit which executes various kinds of information processing can be installed in the connector. The components corresponding to the above-described zoom lens drive control section, focus lens drive control section, and/or image sensor drive control section may be installed in the connector.

The configuration of the imaging device 10 has been described above. The configuration of the imaging device 10 is not, however, limited to this example. The imaging device 10 includes at least the image sensor 105, and the optical system 101 for concentrating observation light on the image sensor 105, and at least one optical member included in the optical system 101 only has to be configured to be drivable for the AF function in the present embodiment. The imaging device 10 may have any specific device configuration. Various known kinds of configuration may be applied as the imaging device 10.

Next, the configuration of the control device 20 will be described. The control device 20 includes the imaging signal processing section 117, the AF control section 118, an AF operation determination section 125, and the zoom operation control section 127 as functions thereof.

The control device 20 corresponds to, for example, a CCU as described above. The control device 20 includes a variety of processors and a storage element such as a memory. Each of the above-described functions of the control device 20 is implemented by a processor included in the control device 20 executing operational processing in accordance with a predetermined program.

The zoom operation control section 127 performs various kinds of control for the zoom operation of the imaging system 1. Specifically, the imaging system 1 can receive an instruction signal (zoom instruction signal) that is issued by a surgeon and indicates that a zoom operation is performed. The zoom instruction signal is input via a variety of input devices such as a switch that are included in the imaging system 1, but not illustrated. The zoom instruction signal also includes an instruction about magnification. The zoom operation control section 127 decides the movement amount of the zoom lens 102 which can offer the instructed magnification on the basis of the zoom instruction signal. Information on the decided movement amount is transmitted to the zoom lens drive control section that is not illustrated. The zoom lens drive control section moves the zoom les 102 via the zoom lens driving section 107 by the decided movement amount, thereby adjusting the magnification of the optical system 101 in accordance with the instruction of the surgeon. Additionally, in a case where an optical member other than the zoom lens 102 is also configured to be movable for adjusting the magnification of the optical system 101, the zoom operation control section 127 may also decide the movement amount of the other optical member on the optical axis.

Additionally, the function of the zoom operation control section 127 may be similar to the function of a typical existing imaging system for adjusting magnification. Accordingly, the function of the zoom operation control section 127 will not be described in more detail here.

The imaging signal processing section 117 performs various kinds of signal processing such as a gamma collection process and a white balance adjustment process on an imaging signal acquired by the image sensor 105 for allowing a display device (not illustrated) to display an object image. The imaging signal (which will be referred to as image signal) subjected to the various signal processing performed by the imaging signal processing section 117 is transmitted to the display device. The display device shows an image of the object on the basis of the image signal. A surgeon can observe the condition of the biological tissue serving as the object via the display device. Further, the imaging signal processing section 117 also provides the image signal to an AF frame decision section 119 of the AF control section 118 which will be described below.

The AF control section 118 performs various kinds of control for the AF operation of the imaging device 10. FIG. 1 illustrates, as an example, the functional components of the AF control section 118 which correspond to a case where the AF method is a contrast method. The contrast method is a method in which a focusing operation is performed by searching for, while moving at least one optical member (focus lens 103 in the illustrated example) included in the optical system 101, the position of the optical member at which the contrast of an object image is maximized, and moving the optical member to the position at which the contrast is maximized.

The AF method applied to the imaging system 1 is not, however, limited in the present embodiment. A variety of known methods may be used as the AF method. An AF method of a passive type can be, however, favorably applied to the imaging system 1 in the present embodiment.

Here, AF methods are roughly categorized into two types in general: an active type; and a passive type. A method of the active type is a method in which the distance to an object is measured by irradiating the object, for example, with near infrared light or the like and receiving the reflected light thereof, and a focusing operation is performed by moving an optical member included in the optical system on the basis of the measured distance in a manner that the object comes into focus. Meanwhile, a method of the passive type is a method in which a focusing operation is performed by radiating no light or the like for measuring distance from the optical system, but moving an optical member included in the optical system on the basis of information acquired from a captured object image in a manner that an object comes into focus.

As described above, the imaging system 1 can be, for example, an endoscopic system. It is, however, difficult for the endoscopic system to adopt the active type as the AF method. This is because the active type requires the endoscope to include a component for measuring distance at the proximal end, which increases the size of the proximal end of the endoscope, and can place a heavier burden on the body of a patient. Even in a case where the imaging system 1 is a microscopic system, it is not preferable to increase the size of the configuration of the microscopic section which images an operative site in order to secure a surgeon a working space. The passive type can be thus applied favorably as the AF method of the imaging system 1 in the present embodiment.

A variety of methods referred to as phase difference method, depth map method, and triangulation method in general are known as addition to the above-described contrast method as AF methods of the passive type. These methods all perform a focusing operation on the basis of information acquired from a captured object image. However, these methods have the characteristic that, in a case where the contrast of the object image is relatively low (in a case of so-called low contrast), it is difficult to normally perform a focusing operation (i.e., it is difficult for an AF operation to bring an object into focus). Such an AF method in which it is difficult to normally perform a focusing operation in a case where an object image has low contrast can also be considered a method in which an AF operation is executed on the basis of contrast. Accordingly, the following description also refers to such an AF method as method based on contrast for the sake of convenience. Many of the AF methods of the passive type are methods based on contrast. Accordingly, it can also be said that the present embodiment targets the imaging system 1 to which a method based on contrast is applied as the AF method.

FIG. 1 will be referred to again, and the function of the AF control section 118 will be continuously described. The AF control section 118 includes the AF frame decision section 119, a contrast detection section 121, and a focus lens movement amount decision section 123 as functions thereof. Additionally, the AF control section 118 executes a series of processes for an AF operation in accordance with an instruction signal (AF instruction signal) which is input by a surgeon and indicates that the AF operation is performed. The AF instruction signal can be input via a variety of input devices such as a switch that are included in the imaging system 1, but not illustrated.

The AF frame decision section 119 generates an object image on the basis of an image signal acquired by the imaging signal processing section 117, and decides, from the object image, an area (AF frame) that comes into focus when an AF operation is performed. The AF frame decision section 119 provides information on the decided AF frame to the contrast detection section 121.

The contrast detection section 121 detects the contrast of the area corresponding to the AF frame decided by the AF frame decision section 119 in the object image. The AF control section 118 regards the contrast of the area corresponding to the AF frame as the contest of the object image, and performs an AF operation. The contrast detection section 121 provides information on the detected contrast of the area corresponding to the AF frame (i.e., contrast of the object image) to the focus lens movement amount decision section 123.

The focus lens movement amount decision section 123 decides the movement amount of the focus lens 103 on the basis of the information on the detected contrast of the object image by the contrast detection section 121. Specifically, the focus lens movement amount decision section 123 decides the movement amount of the focus lens 103 on the basis of the contrast of the object image in the last step and the contrast of the object image in the present step in a manner that the focus lens 103 moves by a predetermined distance on the optical axis in the direction in which the contrast is higher. Additionally, the movement amount of the focus lens 103 only has to be decided in the first step (in a case where there is no information on the contrast of the object image in the last step) in a manner that the focus lens 103 is moved by a predetermined distance in a predetermined direction set in advance.

Information on the decided movement amount of the focus lens 103 is transmitted to the focus lens drive control section that is not illustrated. The focus lens drive control section moves the focus lens 103 via the focus lens driving section 111 by the decided movement amount.

The series of processes described above will be repeatedly executed below, thereby executing an AF operation in the contrast method. That is, the imaging signal processing section 117 generates an image signal on the basis of an imaging signal acquired by the image sensor 105 after the focus lens 103 moves. The AF frame decision section 119, the contrast detection section 121, and the focus lens movement amount decision section 123 execute the above-described processes again on the basis of the image signal, and the focus lens 103 is moved by the focus lens drive control section in accordance with the decided movement amount. The repeated execution of these processes finally moves the focus lens 103 to the position at which the contrast of the object image is maximized. An image that has the object in focus is acquired, and the series of processes for the AF operation is then terminated.

Additionally, in a case where an optical member other than the focus lens 103 is also configured to be movable for adjusting the focal distance of the optical system 101, the focus lens movement amount decision section 123 may also decide the movement amount of the other optical member on the optical axis.

Further, the series of processes (process of deciding the AF frame, process of detecting the contrast, and process of deciding the movement amount of the focus lens 103) described above and performed by the AF control section 118 may be similar to the series of processes performed in an AF operation in the typical existing contrast method. A variety of known methods used for an AF operation in the contrast method may be used as a specific method for each process, and will not be described here in detail. For example, JP 2748637B, which is a prior application filed by the Applicants of the present application, can be seen for the details of an AF operation in the contrast method in detail.

Here, in a case where a method based on the contrast of an object image like the contrast method is applied to the imaging system 1 as the AF method, there is the probability that an AF operation is not normally performed by the AF control section 118 when an object having low contrast is imaged.

Figure 2:
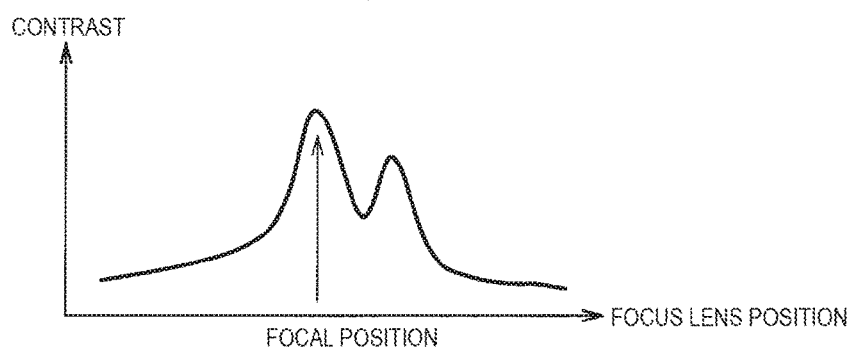
FIG. 2 is an explanatory diagram for describing a concept of an AF operation in a contrast method.
Figure 3:
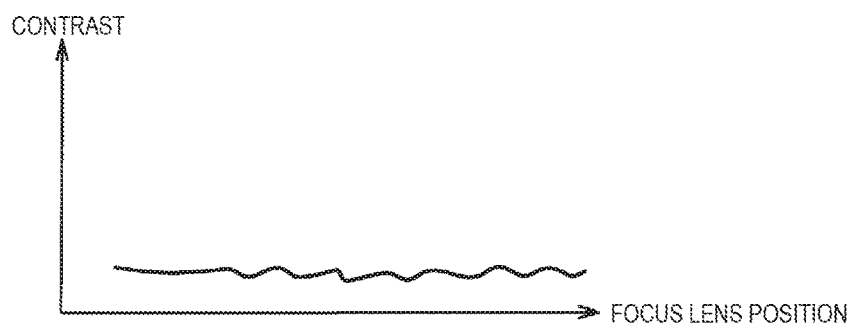
FIG. 3 is an explanatory diagram for describing the concept of the AF operation in the contrast method.

FIGS. 2 and 3 are explanatory diagrams each of which describes the concept of the AF operation in the contrast method. FIG. 2 illustrates an example of the contrast of an object image in a case where an AF operation can be normally executed in the contrast method. As illustrated in FIG. 2, in a case of an object that undergoes a relatively big change in contrast, the position of the focus lens 103 can be relatively easily found out at which the contrast is maximized. An AF operation can be therefore normally executed. Meanwhile, as illustrated in FIG. 3, in a case of an object that undergoes a relatively small change in contrast, it is difficult to find out the position of die focus lens 103 at which the contrast is maximized. There is the probability that an AF operation is not normally performed.

Here, it is assumed in general that biological tissue of a patient such as blood, internal organs, and bones is imaged in the medical imaging system. These kinds of biological tissue have, however, low contrast in many cases. In a case where an AF operation is performed in a method based on contrast, it can be difficult to normally perform the AF operation. For example, a subtle increase or decrease in contract caused by noise or the like can cause an optical member such as a focus lens to move to a wrong position that is not the original focal position. Alternatively, in a case where the contrast method is used, there is the probability that it is difficult to carry out a surgical operation or an inspection because it is not possible to decide the position (i.e., focal position) at which the contrast is maximized, but an optical member such as a focus lens keeps on moving on the optical axis. In this way, failure in normally executing an AF operation in the imaging system can considerably stress a surgeon.

In view of such circumstances, for example, Patent Literature 1 discloses, as existing technology, a microscopic system that has the AF function, and stops, in a case where it is determined that it is not possible to normally execute an AF operation, the AF operation, and moves an optical system to an initial position. The technology described in Patent literature 1, however, returns the optical system to the initial position in a case where it is determined that it is no possible to normally execute an AF operation. As a result, there is a high probability that an image out of focus is acquired. To carry out a surgical operation or an inspection, a surgeon thus needs manual focusing. It cannot be therefore said that the system which is always convenient for a surgeon has been built.

The AF operation determination section 125 then determines in the present embodiment whether it is possible to normally execute an AF operation, namely whether it is possible for an AF operation to bring an object into focus. In a case where it is determined that it is not possible for an AF operation to bring an object into focus, the process for the AF operation in the AF control section 118 is then stopped, and the focus lens 103 is moved to a predetermined position set in advance in accordance with the purpose of imaging. Here, the position of the focus lens 103 at which an object comes into focus in an object distance assumed in accordance with the purpose of imaging can be set on the basis of the object distance as the predetermined position. There is thus a high probability that an image acquired after the focus lens 103 moves to the position is an image that has biological tissue serving as an object in focus. The following description also refers to the predetermined position set in advance in accordance with the purpose of imaging as predicted focal position.

In this way, according to the present embodiment, in a case where it is difficult to normally perform an AF operation, the focus lens 103 moves to a predicted focal position, thereby acquiring a clear image that has biological tissue serving as an object in better focus. A surgeon can thus carry out a surgical operation or an inspection with no additional operation such as focusing. According to the present embodiment, the imaging system 1 that is more convenient can be therefore provided.

An AF operation determination process performed by the AF operation determination section 125, and the following process in the imaging system 1 will be described in more detail. As described above, the AF operation determination section 125 determines whether it is possible to normally execute an AF operation, namely whether it is possible for an AF operation to bring an object into focus (whether it is possible to decide the position of the focus lens 103 at which an AF operation brings an object into focus). Additionally, the AF operation determination process performed by the AF operation determination section 125 can be executed as needed at predetermined intervals while an AF operation is being executed.

In a case where the contrast method is applied like the illustrated configuration example, for example, the AF operation determination section 125 can determine that it is not possible to for an AF operation to bring an object into focus in a case where a predetermined time elapses in the AF operation without deciding the final position of the focus lens 103 (i.e., position of the focus lens 103 at which the contrast of an object image is maximized). Further, for example, in a case where the focus lens 103 arrives a predetermined number of times at an end point of the movable range thereof in an AF operation, the AF operation determination section 125 can determine that it is not possible for the AF operation to bring an object into focus. Alternatively, these determination criteria may be combined and used. That is, in a case where a predetermined time elapses without deciding the position of the focus lens 103 at which the contrast of an object image is maximized, or in a case where the focus lens 103 arrives a predetermined number of times at an end point of the movable range thereof in an AF operation, the AF operation determination section 125 may determine that it is not possible for the AF operation to bring an object into focus.

Additionally, values that can be used in general for the AF operation determination process may be applied as appropriate as the predetermined time and the predetermined number of times. The predetermined time can be, for example, approximately five seconds. Further, the predetermined number of times can be, for example, one time at each end point. Further, the AF operation determination section 125 uses, as a determination criterion of an AF operation, whether the focus lens 103 arrives a predetermined number of times at an end point of the movable range thereof in the AF operation in the above-described example, but may also use, as the determination criterion, whether the focus lens 103 arrives a predetermined number of times at an end point of a specific range included in the movable range thereof in the AF operation. That is, the AF operation determination section 125 may determine whether it is possible to normally execute an AF operation, in accordance with whether the focus lens 103 moves within a part of the movable range thereof in the AF operation without finding out an appropriate focal position.

For example, the AF operation determination section 125 can be provided with information on the decided movement amount of the focus lens 103 and information indicating whether an AF operation is terminated from the focus lens movement amount decision section 125. The AF operation determination section 125 can execute an AF operation determination process as described above on the basis of these kinds of information.

The criterion of the AF operation determination process performed by the AF operation determination section 125 is not, however, limited to this example. A variety of known determination criteria used in general for an AF operation in the contrast method may be used in the present embodiment as a criterion for determining whether it is possible to normally execute an AF operation.

Additionally, in a case where another method is applied as the AF method in the imaging system 1, the AF operation determination section 125 may determine as needed whether it is possible to normally execute an AF operation in the method corresponding to the applied AF method. A variety of methods are known in general as a method for determining whether it is possible to normally execute an AF operation. For example, a variety of methods for determining that an object has so-called low contrast are proposed for a variety of existing imaging devices to which a method based on contrast is applied as the AF method. The AF operation determination section 125 may perform a determination process in a variety of known methods on the basis of the applied AF method.

In a case where the AF operation determination section 125 determines that it is possible for an AF operation to bring an object into focus, the AF control section 118 continues the series of processes described above for the AF operation, namely continues the AF operation.

Meanwhile, in a case where the AF operation determination section 125 determines that it is not possible for an AF operation to bring an object into focus, the AF operation determination section 125 provides information indicating that to the focus lens movement amount decision section 123. In this case, the process for the AF operation in the AF control section 118 is stopped. The focus lens movement amount decision section 123 decides the movement amount of the focus lens 103 so as to move the focus lens 103 to the predicted focal position, and moves the focus lens 103 in accordance with the movement amount via the focus lens drive control section (not illustrated) and the focus lens driving section 111.

As described above, the position of the focus lens 103 at which an object comes into focus in an object distance assumed in accordance with the purpose of imaging can be set as the predicted focal position on the basis of the object distance. The movement of the focus lens 103 to the predicted focal position thus offers an image that has biological tissue serving as an object relatively in focus.

Additionally, the "purpose of imaging" can include a surgical procedure, a clinical department, a preference of a surgeon, and the like. Once the surgical procedure and/or the clinical department is decided, it can be predicted with a high probability in what object distance and what kind of biological tissue is observed. Accordingly, setting the predicted focal position on the basis of the surgical procedure and/or the clinical department makes it possible to set a more appropriate position as the predicted focal position. Further, even in a case where the same biological tissue is observed, the optimum object distance can differ in accordance with preferences of a surgeon. Setting the predicted focal position in accordance with a surgeon who uses the imaging system 1 to observe an operative site can thus build the imaging system 1 that is more convenient for the surgeon.

Further, the predicted focal position may also be set in accordance with the optical property of the optical system attached to the imaging device 10. For example, it is assumed that a different type of endoscope is attached and used in the imaging system 1 in accordance with the purpose of imaging (surgical procedure or the like). In general, an object distance recommended to be used for the endoscope is set in accordance with the type thereof, namely the optical system of the endoscope, in many cases. When the predicted focal position is set, the predicted focal position may be thus set in on the basis of the type of endoscope attached to the imaging device 10 to bring an object into focus in consideration of the object distance that can be set in accordance with the optical system of the endoscope. Additionally, there is another optical system in between in addition to the endoscope, the predicted focal position may also be set in consideration of the optical property of the other optical system. Alternatively, in a case where the imaging system 1 is a microscopic system, and an additional optical system is attached to the microscopic section that can correspond to the imaging device 10, the predicted focal position may also be set in accordance with the optical property of the additional optical system.

Additionally, the predicted focal position may be manually set by a surgeon before a surgical operation in accordance with factors (such as a surgical procedure, a clinical department, a preference of the surgeon, and the optical system of the endoscope) as described above which can decide the predicted focal position. Alternatively, for example, in a case where the predicted focal position can be set in accordance with the type of endoscope, the imaging system 1 may have a function of detecting the type of the attached endoscope. In addition, the predicted focal position may be automatically set in accordance with the type of endoscope on the basis of a detection result of the detection function.

The configuration of the imaging system 1 according to the present embodiment has been described above with reference to FIG. 1. Additionally, the configuration illustrated in FIG. 1 is merely an example. The imaging system 1 may have any specific device configuration as long as the imaging system 1 can execute the above-described processes as a whole. For example, the control device 20 may have some of the functions of the imaging device 10 in FIG. 1. Conversely, the imaging device 10 may have some of the functions of the control device 20.

Alternatively, the functions corresponding to the respective blocks illustrated in FIG. 1 may be distributed in more devices, or a single device may have all of the functions. For example, FIG. 1 illustrates the configuration corresponding to an endoscopic system as an example of the imaging system 1, but the imaging system 1 may also be a microscopic system in the present embodiment. In a case where the imaging system 1 is a microscopic system, the illustrated components can be all installed in a single device to constitute the imaging system 1.

Further, it is possible to manufacture a computer program for executing the functions of the imaging system 1 according to the present embodiment as described above, and implement the manufactured computer program in an information processing device such as a personal computer (PC). Further, there can also be provided a computer-readable recording medium having such a computer program stored therein. Examples of the recording medium include a magnetic disk, an optical disc, a magneto-optical disk, and a flash memory. The computer program may also be distributed via a network, for example, using no recording medium.

(2. Imaging Method)

Figure 4:
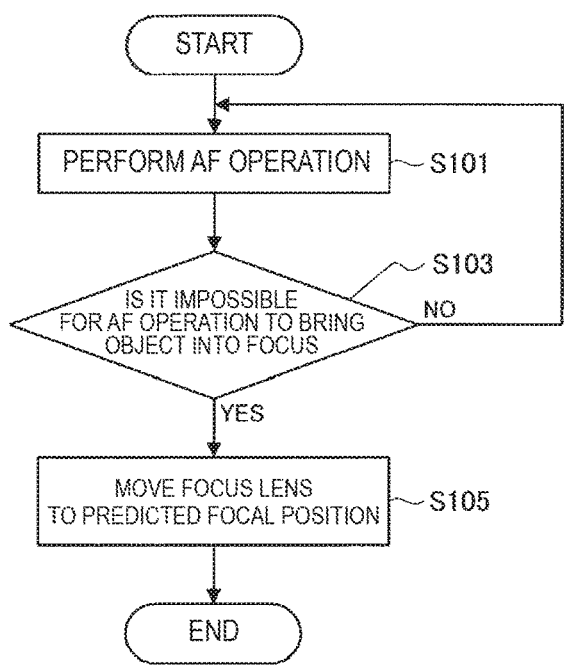
FIG. 4 is a flowchart illustrating an example of a procedure of an imaging method according to the present embodiment.

A procedure of an imaging method executed by the above-described imaging system 1 will be described with reference to FIG. 4. FIG. 4 is a flowchart illustrating an example of the procedure of the imaging method according to the present embodiment.

Additionally, a process characteristic of the present embodiment in the focusing operation process for bringing an object into focus is executed among the series of processes for imaging the object in the imaging method according to the present embodiment. FIG. 4 thus illustrates a procedure of the focusing operation process among the series of processes in the imaging method according to the present embodiment. The series of processes illustrated in FIG. 4 are processes that can be executed, for example, in a case where a surgeon inputs an AF instruction signal.

Additionally, the series of processes illustrated in FIG. 4 are actually executed in the imaging system 1 while an image signal is being acquired. An image that has an object in focus is hereby acquired. That is, a process of acquiring an image signal on the basis of an imaging signal (corresponding to the process executed by the imaging signal processing section 117 illustrated in FIG. 1) is executed before the process in step S101 illustrated in FIG. 4.

FIG. 4 illustrates that, for example, the input of the AF instruction signal first serves as a trigger and an AF operation is executed in the focusing operation process in the imaging method according to the present embodiment (step S101). For example, in a case where the contrast method is applied, a process of searching for, while moving the focus lens 103, the position of the focus lens 103 at which the contrast of an object image is maximized is executed in step S103. The process corresponds to the processes executed by the AF control section 118 illustrated in FIG. 1, the focus lens drive control section (not illustrated), and the focus lens driving section 111. The present embodiment is not, however, limited to this example. In step S103, an AF operation based on other various types of AF methods may be executed.

Next, it is determined in the AF operation whether it is possible to normally execute the AF operation, namely whether it is possible for the AF operation to bring an object into focus (step S103). Specifically, in step S103, it can be determined whether it is possible for the AF operation to bring an object into focus in the method corresponding to the method of the AF operation executed in step S101.

For example, in a case where the contrast method is applied, if is determined in step S103 that if is not possible for the AF operation to bring the object into focus, in a case where a predetermined time elapses without deciding the position of the focus lens 103 at which the contrast of the object image is maximized in the AF operation, or in a case where the focus lens 103 arrives at a predetermined number of times at an end point of the movable range thereof in the AF operation. In the other cases, it is determined that it is possible for the AF operation to bring the object into focus.

The present embodiment is not, however, limited to this example. In step S103, a process of determining whether it is possible to execute an AF operation performed in general in a variety of AF methods may be executed. Additionally, the process in step S103 corresponds to the process executed by the AF operation determination section 125 illustrated in FIG. 1.

The determination process in step S103 can be executed as needed at predetermined intervals in the AF operation. In a case where it is determined in step S103 that it is possible for the AF operation to bring the object into focus, the processing returns to step S101 and the AF operation is continued. It is then determined again in step S103 after predetermined intervals whether it is possible for the AF operation to bring the object into focus. In a case where the AF operation is normally terminated while the processes in step S101 and step S103 are being repeatedly executed, namely in a case where the object accurately comes into focus, the series of processes in the imaging method according to the present embodiment are also terminated.

Meanwhile, in a case where it is determined in step S103 that it is not possible for the AF operation to bring the object into focus, the processing proceeds to step S105. In step S105, the focus lens 103 is moved to a predetermined position (predicted focal position) set in advance in accordance with the purpose of imaging. The position of the at focus lens 103 at which an object comes into focus in an object distance assumed in accordance with the purpose of imaging can be set as the predicted focal position on the basis of the object distance. Additionally, the process illustrated in step S105 corresponds to the processes executed by the focus lens movement amount decision section 123 illustrated in FIG. 1, the focus lens drive control section (not illustrated and the focus lens driving section 111.

Once the focus lens 103 is moved in step S105 to the predicted focal position, the series of processes in the imaging method according to the present embodiment are terminated. In this way, in a case where it is determined that it is not possible to normally execute an AF operation, the focus lens 103 is moved to the predicted focal position. This makes it possible to acquire a clear image that is relatively in focus without requiring an additional operation of a surgeon for focusing. In addition, it is possible to improve the convenience of the surgeon.

The procedure of the imaging method according to the present embodiment has been described with reference to FIG. 4.

(3. Modifications)

Some modifications of the above-described embodiment will be described. Additionally, each of the modifications described below corresponds to the above-described embodiment in which the AF method is changed.

(3-1. Case where Phase Difference Method is used)

A case where a phase difference method is used as the AF method in the imaging system 1 illustrated in FIG. 1 will be described. The phase difference method is a method in which a focusing operation is performed by calculating the distance to an object on the basis of the image interval between two object images acquired by causing observation light to form images at different positions in the light receiving surface, and moving the focus lens 103 on the basis of the calculated distance to the object to bring the object into focus.

Figure 5:
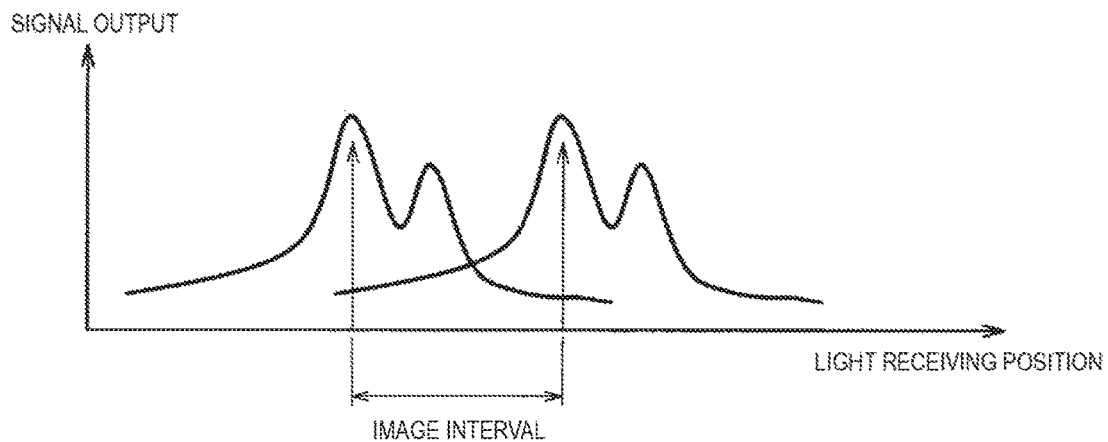
FIG. 5 is an explanatory diagram for describing a concept of an AF operation in a phase difference method.
Figure 6:
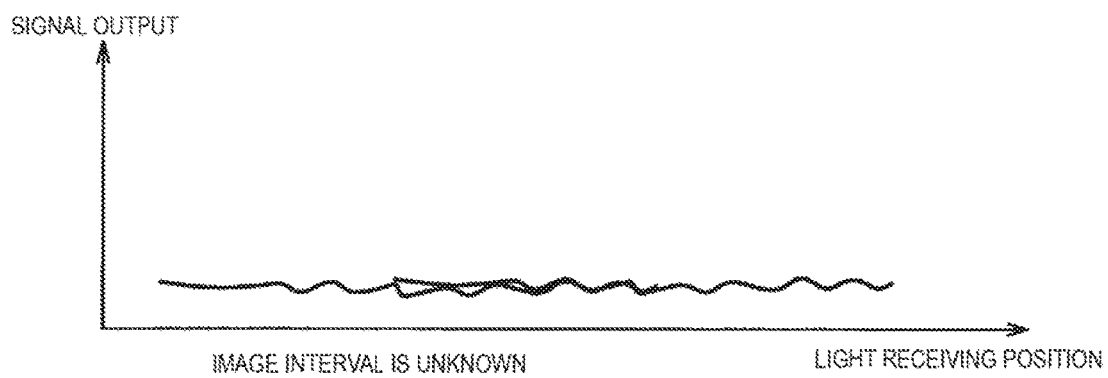
FIG. 6 is an explanatory diagram for describing the concept of the AF operation in the phase difference method.

FIGS. 5 and 6 are explanatory diagrams each of which describes the concept of the AF operation in the phase difference method. FIG. 5 illustrates an example of the contrast of an object image in a case where an AF operation can be normally executed in the phase difference method. As illustrated in FIG. 5, in a case of an object having relatively high contrast, it is possible to relatively clearly detect the image interval between two object images. Accordingly, it is possible to calculate the distance to the object on the basis of the image interval, and execute an AF operation.

Meanwhile, as illustrated in FIG. 6, in a case of an object having relatively low contrast, it is difficult to acquire the relationship between two object images and detect the image interval between the two object images. It is therefore not possible to calculate the distance to the object. In addition, there is the probability that an AF operation is not normally performed.

In this way, similarly to the above-described embodiment, there is the probability that it is not possible to normally execute an AF operation on an object having low contrast in the phase difference method. In a case where the phase difference method is used, the imaging system that is convenient for a surgeon can be thus built by configuring the imaging system in a manner that the focus lens is moved to the predicted focal position in a case where it is determined that it is not possible for an AF operation to bring an object into focus.

The imaging system to which the phase difference method is applied as the AF method corresponds to the configuration of the imaging system 1 illustrated in FIG. 1 in which the function of the AF control section 118 for an AF operation and the determination criterion of the AF operation determination section 125 are changed. Specifically, for example, the AF control section 118 illustrated in FIG. 1 executes, as processes for an AF operation, a process of acquiring the image interval between two object images, a process of calculating the distance to an object on the basis of the image interval, and a process of calculating, on the basis of the calculated distance to the object, the movement amount of the focus lens 103 to the position at which the object comes into focus in the imaging system to which the phase difference method is applied. Further, for example, the AF operation determination section 125 determines whether it is possible for an AF operation to bring an object into focus in a variety of methods used in general for an AF operation in the phase difference method.

Additionally, in a case where the phase difference method is used, there may be provided another image sensor for measuring distance in the imaging device 10 in addition to the image sensor 105 for imaging. In addition, an AF operation may also be performed on the basis of two object images acquired by the other image sensor. Alternatively, an area for measuring distance may be secured in a part of the light receiving surface of the image sensor 105, and an AF operation may be performed on the basis of two object images acquired on the light receiving surface corresponding to the area for measuring distance. In this case, the single image sensor 105 can both image an object and measure distance for an AF operation. Accordingly, it is possible to further simplify the configuration of the imaging device 10.

(3-2. Case where Depth Map Method is used)

A case where a so-called depth map method is used as the AF method in the imaging system 1 illustrated in FIG. 1 will be described. The depth map method is an AF method that uses space recognition technology, and is a method in which a focusing operation is performed by calculating the distance to an object on the basis of the blurring degree (defocus degree) of an object image and moving the focus lens 103 on the basis of the calculated distance to the object in a manner that the object comes into focus.

Here, it is known that it is difficult to accurately detect the defocus degree for an object having low contrast. That is, similarly to the above-described embodiment, there is the probability that it is not possible to normally execute an AF operation on an object having low contrast in the depth map method. In a case where the depth map method is used, the imaging system that is convenient for a surgeon can be thus built by configuring the imaging system in a manner that the focus lens is moved to the predicted focal position in a case where it is determined that it is not possible for an AF operation to bring an object into focus.

The imaging system to which the depth map method is applied as the AF method corresponds to the configuration of the imaging system 1 illustrated in FIG. 1 in which the function of the AF control section 118 for an AF operation and the determination criterion of the AF operation determination section 125 are changed. Specifically, for example, the AF control section 118 illustrated in FIG. 1 executes, as processes for an AF operation, a process of detecting the defocus degree of an object image, a process of calculating the distance to an object on the basis of the detected defocus degree of the object image, and a process of calculating, on the basis of the calculated distance to the object, the movement amount of the focus lens 103 to the position at which the object comes into focus in the imaging system to which the depth map method is applied. Further, for example, the AF operation determination section 125 determines whether it is possible for an AF operation to bring an object into focus in a variety of methods used in general for an AF operation in the depth map method.

(3-3. Case where Triangulation Method is used)

A case where a so-called triangulation method is used as the AF method in the imaging system 1 illustrated in FIG. 1 will be described. The triangulation method is an AF method in which 3D stereogram technology is used, and a focusing operation is performed by calculating the distance to an object in accordance with the principle of triangulation on the basis of the disparity information acquired from two object images acquired by causing observation light to form images at different positions in the light receiving surface, and moving the focus lens 103 on the basis of the calculated distance to the object to bring the object into focus.

Here, it is difficult to acquire the relationship between two object images for an object having low contrast and accurately acquire disparity information. That is, similarly to the above-described embodiment, there is the probability that it is not possible to normally execute an AF operation on an object having low contrast in the triangulation method. In a case where the triangulation method is used, the imaging system that is convenient for a surgeon can be thus built by configuring the imaging system in a manner that the focus lens is moved to the predicted focal position in a case where it is determined that it is not possible for an AF operation to bring an object into focus.

The imaging system to which the triangulation method is applied as the AF method corresponds to the configuration of the imaging system 1 illustrated in FIG. 1 in which the function of the AF control section 118 for an AF operation and the determination criterion of the AF operation determination section 125 are changed. Specifically, for example, the AF control section 118 illustrated in FIG. 1 executes, as processes for an AF operation, a process of acquiring disparity information from two object images, a process of calculating the distance to an object on the basis of the principle of triangulation on the basis of the disparity information and the baseline distance (distance between the light receiving elements corresponding to the positions at which the two object images are formed), and a process of calculating, on the basis of the calculated distance to the object, the movement amount of the focus lens 103 to the position at which the object comes into focus in the imaging system to which the triangulation method is applied. Further, for example, the AF operation determination section 125 determines whether it is possible for an AF operation to bring an object into focus in a variety of methods used in general for an AF operation in the triangulation method.

Additionally, in a case where the triangulation method is used, there may be provided another image sensor for measuring distance in the imaging device 10 in addition to the image sensor 105 for imaging. In addition, an AF operation may also be performed on the basis of two object images acquired by the other image sensor. Alternatively, an area for measuring distance may be secured in a part of the light receiving surface of the image sensor 105, and an AF operation may be performed on the basis of two object images acquired on the light receiving surface corresponding to the area for measuring distance. In this case, the single image sensor 105 can both image an object and measure distance for an AF operation. Accordingly, it is possible to further simplify the configuration of the imaging device 10.

(4. Supplemental Information)

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A control device including:
an autofocus control section configured to execute an autofocus operation by moving at least one optical member; and
an autofocus operation determination section configured to determine whether it is possible for the autofocus operation to bring biological tissue into focus, the biological tissue serving as an object, in which
in a case where the autofocus operation determination section determines that it is not possible for the autofocus operation to bring the object into focus, the autofocus control section moves the at least one optical member to a predicted focal position set in advance in accordance with a purpose of imaging.

(2)
The control device according to (1), in which
the predicted focal position is set in accordance with a surgical procedure of a surgical operation in which the object is imaged.

(3)
The control device according to (1) or (2), in which
the predicted focal position is set in accordance with a clinical department in which the object is imaged.

(4)
The control device according to any one of (1) to (3), in which
it is possible to set the predicted focal position in accordance with a surgeon who observes the object that is imaged.

(5)
The control device according to any one of (1) to (4), in which
the predicted focal position is set in accordance with an optical property of an optical system attached to an imaging device that is connected to the control device.

(6)
The control device according to any one of (1) to (5), in which
the autofocus operation is executed on the basis of contrast of an object image.

(7)
The control device according to (6), in which
the autofocus operation is an operation of focusing by searching for, while moving the at least one optical member, a position at which the contrast of the object image is maximized, and moving the at least one optical member to the position at which the contrast is maximized.

(8)
The control device according to (7), in which
in a case where a predetermined time elapses in the autofocus operation without deciding the position of the at least one optical member at which the contrast of the object image is maximized, it is determined that it is not possible for the autofocus operation to bring the object into focus, and the at least one optical member moves to the predicted focal position.

(9)
The control device according to (7) or (8), in which
in a case where the at least one optical member arrives a predetermined number of times at an end point of a specific range included in a movable range in the autofocus operation, it is determined that it is not possible for the autofocus operation to bring the object into focus, and the at least one optical member moves to the predicted focal position.

(10)
The control device according to (6), in which
the autofocus operation is an operation of focusing by calculating a distance to the object on the basis of an image interval between two object images acquired by causing light from the object to form images at different positions in a light receiving surface, and moving the at least one optical member on the basis of the distance.

(11)
The control device according to (6), in which
the autofocus operation is an operation of focusing by calculating a distance to the object on the basis of a defocus degree of the object image, and moving the at least one optical member on the basis of the distance.

(12)
The control device according to (6), in which
the autofocus operation is an operation of focusing by calculating a distance to the object in accordance with a principle of triangulation on the basis of disparity information acquired from two object images acquired by causing light from the object to form image at different positions in a light receiving surface, and moving the at least one optical member on the basis of the distance.

(13)
A medical imaging system including:
an image sensor configured to image biological tissue serving as an object;
an optical system configured to concentrate light from the object on the image sensor, and configured in a manner that at least one optical member is movable on an optical axis for a focusing operation;
an autofocus control section configured to execute an autofocus operation by moving the at least one optical member; and
an autofocus operation determination section configured to determine whether it is possible for the autofocus operation to bring the object into focus, in which
in a case where the autofocus operation determination section determines that it is not possible for the autofocus operation to bring the object into focus, the autofocus control section moves the at least one optical member to a predicted focal position set in advance in accordance with a purpose of imaging.

REFERENCE SIGNS LIST 1 imaging system
10 imaging device
20 control device
101 optical system
102 zoom lens
103 focus lens
105 image sensor
107 zoom lens driving section
111 focus lens driving section
115 image sensor driving section
117 imaging signal processing section
118 AF control section
119 AF frame decision section
121 contrast detection section
123 focus lens movement amount decision section
125 AF operation determination section
127 zoom operation control section

The invention claimed is:

1. A control device comprising:
processing circuitry configured to
execute an autofocus operation on the basis of contrast of an object in an object image, by moving at least one optical member,
obtain, from a medical imaging device, contrast data of the object in the object image, and
determine, based upon whether the contrast data satisfies a predetermined condition, whether it is possible for the autofocus operation to bring the object in the object image into focus,
wherein, in a case where it is determined that it is not possible for the autofocus operation to bring the object in the object image into focus, the at least one optical member is moved to a predicted focal position set in advance in accordance with a purpose of imaging, and
wherein, in a case where a predetermined time elapses in the autofocus operation without deciding a position of the at least one optical member, it is determined that it is not possible for the autofocus operation to bring the object in the object image into focus and the at least one optical member is moved to the predicted focal position set in advance in accordance with the purpose of imaging.

2. The control device according to claim 1, wherein the predicted focal position is set in accordance with a surgical procedure of a surgical operation in which the object is imaged.

3. The control device according to claim 1, wherein the predicted focal position is set in accordance with a clinical department in which the object is imaged.

4. The control device according to claim 1, wherein it is possible to set the predicted focal position in accordance with a surgeon who observes the object that is imaged.

5. The control device according to claim 1, wherein the predicted focal position is set in accordance with an optical properly of an optical system attached to an imaging device that is connected to the control device.

6. The control device according to claim 1, wherein the autofocus operation is an operation of focusing by searching for, while moving the at least one optical member, a position at which the contrast of the object in the object image satisfies a criterion, and moving the at least one optical member to the position at which the contrast satisfies the criterion.

7. The control device according to claim 1, wherein the autofocus operation is an operation of focusing by calculating a distance to the object on the basis of an image interval between two object images acquired by causing light from the object to for s images at different positions in a light receiving surface, and moving the at least one optical member on the basis of the distance.

8. The control device according to claim 1, wherein the autofocus operation is an operation of focusing by calculating a distance to the object on the basis of a defocus degree of the object image, and moving the at least one optical member on the basis of the distance.

9. The control device according to claim 1, wherein the autofocus operation is an operation of focusing by calculating a distance to the object in accordance with a principle of triangulation on the basis of disparity information acquired from two object images acquired by causing light from the object to form images at different positions in a light receiving surface, and moving the at least one optical member on the basis of the distance.

10. A medical imaging system comprising:
an image sensor configured to image biological tissue serving as an object;
an optical system configured to concentrate light from the object on the image sensor, and configured in a manner that at least one optical member is movable on an optical axis for a focusing operation; and
processing circuitry configured to
execute an autofocus operation by moving the at least one optical member, and
determine whether it is possible for the autofocus operation to bring the object into focus,
wherein, in a case where it is determined that it is not possible for the autofocus operation to bring the object into focus, the at least one optical member is moved to a predicted focal position set in advance in accordance with a purpose of imaging, and
wherein, in a case where a predetermined time elapses in the autofocus operation without deciding a position of the at least one optical member, it is determined that it is not possible for the autofocus operation to bring the object into focus and the at least one optical member is moved to the predicted focal position set in advance in accordance with the purpose of imaging.

11. A control device comprising:
processing circuitry configured to
execute an autofocus operation on the basis of contrast of an object in an object image, by moving at least one optical member,
obtain, from a medical imaging device, contrast data of the object in the object image, and
determine, based upon whether the contrast data satisfies a predetermined condition, whether it is possible for the autofocus operation to bring the object in the object image into focus,
wherein, in a case where it is determined that it is not possible for the autofocus operation to bring the object in the object image into focus, the at least one optical member is moved to a predicted focal position set in advance in accordance with a purpose of imaging, and
wherein, in a case where the at least one optical member arrives a predetermined number of times at an end point of a specific range included in a movable range in the autofocus operation, it is determined that it is not possible for the autofocus operation to bring the object in the object image into focus, and the at least one optical member is moved to the predicted focal position set in advance in accordance with the purpose of imaging.

12. The control device according to claim 11, wherein the predicted focal position is set in accordance with a surgical procedure of a surgical operation in which the object is imaged.

13. The control device according to claim 11, wherein the predicted focal position is set in accordance with a clinical department in which the object is imaged.

14. The control device according to claim 11, wherein it is possible to set the predicted focal position in accordance with a surgeon who observes the object that is imaged.

15. The control device according to claim 11, wherein the predicted focal position is set in accordance with an optical property of an optical system attached to an imaging device that is connected to the control device.

16. The control device according to claim 11, wherein the autofocus operation is an operation of focusing by searching for, while moving the at least one optical member, a position at which the contrast of the object in the object image satisfies a criterion, and moving the at least one optical member to the position at which the contrast satisfies the criterion.

17. The control device according to claim 16, wherein the criterion is a maximum.

18. A control device comprising:
processing circuitry configured to
execute an autofocus operation on the basis of contrast of an object in an object image, by moving at least one optical member,
obtain, from a medical imaging device, contrast data of the object in the object image, and
determine, based upon whether the contrast data satisfies a predetermined condition, whether it is possible for the autofocus operation to bring the object in the object image into focus, wherein in a case where it is determined that it is not possible for the autofocus operation to bring the object in the object image into focus, the at least one optical member is moved to a predicted focal position set in advance in accordance with a purpose of imaging, in a case where it is determined that it is possible for the autofocus operation to bring the object in the object image into focus, the at least one optical member is moved to a position based on the autofocus operation, and in a case where a predetermined time elapses in the autofocus operation without deciding a position of the at least one optical member, it is determined that it is not possible for the autofocus operation to bring the object in the object image into focus and the at least one optical member is moved to the predicted focal position set in advance in accordance with the purpose of imaging.

19. The control device according to claim 1, wherein the at least one optical member is moved by a motor.

20. The control device according to claim 11, wherein the at least one optical member is moved by a motor.

* * * * *